(12) United States Patent
Alghufaili et al.

(10) Patent No.: US 11,976,770 B2
(45) Date of Patent: May 7, 2024

(54) SOLID REMOVAL IN GLYCOL RECLAMATION

(71) Applicant: Saudi Arabian Oil Company, Dhahran (SA)

(72) Inventors: Mohammad Abdullah Alghufaili, Ras Tanura (SA); Saleh Saad Alqahtani, Ras Tanura (SA); Byron John Bjorch Andersen, Ras Tanura (SA)

(73) Assignee: Saudi Arabian Oil Company, Dhahran (SA)

( * ) Notice: Subject to any disclaimer, the term of this patent is extended or adjusted under 35 U.S.C. 154(b) by 322 days.

(21) Appl. No.: 17/036,304

(22) Filed: Sep. 29, 2020

(65) Prior Publication Data

US 2022/0099233 A1    Mar. 31, 2022

(51) Int. Cl.
*F16L 55/24*    (2006.01)
*B01D 29/11*    (2006.01)
*B01D 35/02*    (2006.01)

(52) U.S. Cl.
CPC ............ *F16L 55/24* (2013.01); *B01D 29/117* (2013.01); *B01D 35/02* (2013.01)

(58) Field of Classification Search
None
See application file for complete search history.

(56) References Cited

U.S. PATENT DOCUMENTS

| | | | | |
|---|---|---|---|---|
| 1,424,197 A | * | 8/1922 | Gebhard | B01D 35/02 210/303 |
| 1,809,429 A | * | 6/1931 | Sturgis | B01D 35/02 210/312 |
| 2,697,523 A | * | 12/1954 | Bloksma | B01D 46/48 210/166 |
| 2,812,034 A | * | 11/1957 | McKelvey, Jr. | B01D 45/02 55/DIG. 25 |

(Continued)

FOREIGN PATENT DOCUMENTS

| | | |
|---|---|---|
| EP | 1281424 | 2/2003 |
| EP | 2405064 | 1/2012 |

(Continued)

OTHER PUBLICATIONS

PCT International Search Report and Written Opinion in International Appln. No. PCT/US2021/052472, dated Jan. 18, 2022, 15 pages.

(Continued)

*Primary Examiner* — Robert J Popovics
(74) *Attorney, Agent, or Firm* — Fish & Richardson P.C.

(57) ABSTRACT

A solids removal apparatus for glycol reclamation includes a first tubular, a second tubular, and a strainer. The first tubular includes an open end configured to receive a brine stream including solid material. The second tubular is connected to and protrudes from the first tubular. The second tubular is configured to discharge an outlet stream. The strainer is disposed within the second tubular. The strainer is configured to prevent at least a portion of the solid material (Continued)

from flowing through the strainer, such that the outlet stream discharging from the second tubular has a solids content that is less than a solids content of the brine stream.

5 Claims, 4 Drawing Sheets

(56) References Cited

U.S. PATENT DOCUMENTS

| | | | | |
|---|---|---|---|---|
| 3,025,928 | A * | 3/1962 | Heath | E21B 43/34 |
| | | | | 96/184 |
| 3,255,574 | A * | 6/1966 | Glasgow | B01D 17/042 |
| | | | | 96/186 |
| 3,917,474 | A * | 11/1975 | Heckenkamp | B01D 46/003 |
| | | | | 55/330 |
| 4,744,896 | A * | 5/1988 | James | B01D 29/15 |
| | | | | 210/170.07 |
| 5,904,843 | A * | 5/1999 | Herbst | B01D 29/6476 |
| | | | | 210/414 |
| 7,550,077 | B2 * | 6/2009 | Graf | E04D 13/08 |
| | | | | 52/12 |
| 8,133,300 | B1 * | 3/2012 | Gonsalves, III | B01D 19/0042 |
| | | | | 95/254 |
| 8,329,963 | B2 * | 12/2012 | Chen | C07C 29/88 |
| | | | | 422/187 |
| 8,652,304 | B2 * | 2/2014 | Nazzer | C10L 3/10 |
| | | | | 159/901 |
| 9,095,799 | B1 | 8/2015 | Packard | |
| 9,150,477 | B1 | 10/2015 | Lee et al. | |
| 9,272,972 | B2 * | 3/2016 | Lee | B01D 1/30 |
| 9,433,875 | B2 * | 9/2016 | Phelps | C07C 29/76 |
| 9,469,585 | B2 * | 10/2016 | Bussell | B01J 19/24 |
| 9,522,865 | B2 * | 12/2016 | Lee | C07C 29/76 |
| 9,630,122 | B2 * | 4/2017 | Lee | C07C 29/80 |
| 9,725,388 | B2 * | 8/2017 | Bussell | C10L 3/107 |
| 9,790,153 | B2 * | 10/2017 | Caires Fernandez | B01D 1/30 |
| 9,914,685 | B2 * | 3/2018 | Lee | B01D 21/267 |
| 10,252,182 | B2 * | 4/2019 | Lee | C07C 29/80 |
| 10,533,812 | B2 * | 1/2020 | Baxter | B01D 1/16 |
| 10,683,219 | B2 * | 6/2020 | Messenger | B01D 9/0054 |
| 10,934,237 | B2 * | 3/2021 | Messenger | B01D 3/009 |
| 11,052,325 | B2 * | 7/2021 | Seo | B01D 3/148 |
| 11,058,968 | B2 * | 7/2021 | Lee | B01D 3/065 |
| 11,203,560 | B2 * | 12/2021 | Caires Fernandez | |
| | | | | B01D 9/0063 |
| 2010/0191023 | A1 * | 7/2010 | Chen | B01D 9/0054 |
| | | | | 422/187 |
| 2013/0118989 | A1 * | 5/2013 | Caires Fernandez | |
| | | | | B01D 9/0059 |
| | | | | 210/723 |
| 2014/0058140 | A1 * | 2/2014 | Phelps | B01D 15/00 |
| | | | | 210/259 |
| 2015/0225323 | A1 | 8/2015 | Bussell et al. | |
| 2015/0284272 | A1 * | 10/2015 | Messenger | C02F 1/5245 |
| | | | | 210/726 |
| 2016/0002130 | A1 * | 1/2016 | Bussell | C07C 29/76 |
| | | | | 422/187 |
| 2016/0023977 | A1 * | 1/2016 | Lee | B01D 3/143 |
| | | | | 202/175 |
| 2017/0015612 | A1 * | 1/2017 | Bussell | B01D 61/16 |
| 2017/0129835 | A1 * | 5/2017 | Arumugam | C09K 8/035 |
| 2017/0233317 | A1 * | 8/2017 | Lee | B01D 3/143 |
| | | | | 568/868 |
| 2019/0128603 | A1 * | 5/2019 | Baxter | B01D 53/265 |
| 2020/0308029 | A1 * | 10/2020 | Messenger | C02F 1/5245 |
| 2022/0099233 | A1 * | 3/2022 | Alghufaili | B01D 29/117 |

FOREIGN PATENT DOCUMENTS

| | | |
|---|---|---|
| WO | WO 2009017971 | 2/2009 |
| WO | WO 2017052377 | 3/2017 |

OTHER PUBLICATIONS

PCT International Preliminary Report on Patentability in International Appln. No. PCT/US2021/052472, dated Apr. 13, 2023, 9 pages.

* cited by examiner

– 1 –
SOLID REMOVAL IN GLYCOL RECLAMATION

TECHNICAL FIELD

This disclosure relates to removal of solids in glycol reclamation.

BACKGROUND

Ethylene glycol (MEG) is commonly used as a hydrate inhibition reagent in hydrocarbon carrying pipelines. Dissolved salts in formation water, pipeline production chemicals, and pipe scale can potentially scale and/or foul piping and equipment. MEG reclamation and regeneration can include removal of such salts and other solid material to mitigate the negative effects of scaling and fouling.

SUMMARY

This disclosure describes technologies relating to the removal of solids in ethylene glycol reclamation. Certain aspects of the subject matter described can be implemented as a solids removal apparatus for glycol reclamation. The apparatus includes a first tubular, a second tubular, and a strainer. The first tubular includes an open end, a closed end opposite the open end, and a wall spanning from the open end to the closed end. The open end is configured to receive a brine stream from a reclaimer flash drum of an ethylene glycol reclaimer unit. The brine stream includes solid material. The wall defines an opening on a lateral surface of the wall. The second tubular is connected to the opening. The second tubular protrudes from the first tubular. The second tubular has an inner diameter that is less than an inner diameter of the first tubular. The second tubular is configured to discharge an outlet stream. The strainer is disposed within the second tubular. The strainer is configured to prevent at least a portion of the solid material from flowing through the strainer, such that the outlet stream discharging from the second tubular has a solids content that is less than a solids content of the brine stream.

This, and other aspects, can include one or more of the following features.

In some implementations, the strainer defines perforations sized to allow solid material having a maximum dimension of up to approximately 1 millimeter (mm) to pass through the strainer while preventing solid material having a dimension of greater than approximately 1 mm from passing through the strainer. In some implementations, the second tubular is in fluid communication with the reclaimer flash drum, such that the solid material having the maximum dimension of up to approximately 1 mm is allowed to flow to the reclaimer flash drum with the outlet stream.

In some implementations, the apparatus includes a flow line from the second tubular to the reclaimer flash drum. In some implementations, the flow line is configured to flow the outlet stream from the second tubular to the reclaimer flash drum. In some implementations, the flow line includes a nozzle configured to supply make-up water downstream of the strainer. In some implementations, the make-up water has a solids content that is less than the solids content of the brine stream.

In some implementations, the solids content of the make-up water is less than the solids content of the outlet stream.

In some implementations, the nozzle is configured to connect to a flush pump for backflow flushing of the first tubular.

In some implementations, the inner diameter of the first tubular is at least approximately 8 inches.

In some implementations, a ratio of a flow rate of the brine stream to the inner diameter of the first tubular is in a range of from approximately 3 gallons per minute per foot (gpm/ft) to approximately 12 gpm/ft.

Certain aspects of the subject matter described can be implemented as a glycol reclamation system. The system includes a reclaimer flash drum and a solids removal apparatus. The apparatus includes a first tubular, a second tubular, and a strainer. The first tubular includes an open end, a closed end opposite the open end, and a wall spanning from the open end to the closed end. The open end is in fluid communication with the reclaimer flash drum and is configured to receive a brine stream from the reclaimer flash drum. The brine stream includes solid material. The wall defines an opening on a lateral surface of the wall. The second tubular is connected to the opening. The second tubular protrudes from the first tubular. The second tubular has an inner diameter that is less than an inner diameter of the first tubular. The second tubular is in fluid communication with the reclaimer flash drum. The strainer is disposed within the second tubular. The strainer is configured to prevent at least a portion of the solid material from flowing through the strainer, such that an outlet stream discharging from the second tubular and flowing to the reclaimer flash drum has a solids content that is less than a solids content of the brine stream.

This, and other aspects, can include one or more of the following features.

In some implementations, the strainer defines perforations sized to allow solid material having a maximum dimension of up to approximately 1 millimeter (mm) to pass through the strainer while preventing solid material having a dimension of greater than approximately 1 mm from passing through the strainer, such that the solid material having the maximum dimension of up to approximately 1 mm is allowed to flow to the reclaimer flash drum with the outlet stream.

In some implementations, the system includes a flow line from the second tubular to the reclaimer flash drum. In some implementations, the flow line includes a nozzle configured to supply make-up water downstream of the strainer. In some implementations, the make-up water has a solids content that is less than the solids content of the brine stream.

In some implementations, the solids content of the make-up water is less than the solids content of the outlet stream.

In some implementations, the system includes a flush pump configured to connect to the nozzle for backflow flushing of the first tubular.

In some implementations, the inner diameter of the first tubular is at least approximately 8 inches.

In some implementations, a ratio of a flow rate of the brine stream to the inner diameter of the first tubular is in a range of from approximately 3 gpm/ft to approximately 12 gpm/ft.

Certain aspects of the subject matter described can be implemented as a method. A brine stream is flowed from a reclaimer flash drum of an ethylene glycol reclaimer unit to a first tubular. The brine stream includes solid material. The brine stream is flowed from the first tubular to a second tubular that is connected to an opening defined on a lateral surface of the first tubular and protruding from the first tubular. At least a portion of the solid material is prevented, by a strainer disposed within the second tubular, from flowing through the strainer as the brine stream flows through the strainer. An outlet stream is discharged from the second tubular. The outlet stream has a solids content that is less than a solids content of the brine stream. The outlet stream is flowed to the reclaimer flash drum.

This, and other aspects, can include one or more of the following features.

In some implementations, the strainer defines perforations that allow solid material having a maximum dimension of up to approximately 1 millimeter (mm) to pass through the strainer while preventing solid material having a dimension greater than approximately 1 mm from passing through the strainer.

In some implementations, make-up water is flowed to a flow line connecting the second tubular to the reclaimer flash drum. In some implementations, the make-up water has a solids content that is less than the solids content of the brine stream.

In some implementations, the solids content of the make-up water is less than the solids content of the outlet stream.

In some implementations, the first tubular is backflow flushed using the flow line.

In some implementations, flowing the brine stream to the first tubular includes flowing the brine stream at a flow rate that satisfies a ratio of the flow rate to an inner diameter of the first tubular being in a range of from approximately 3 gpm/ft to approximately 12 gpm/ft.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

The technology generally relates to solids removal, and in particular, solids removal for ethylene glycol reclamation. An apparatus including a large bore pipe and a strainer is provided in an ethylene glycol (MEG) reclamation unit. The large bore pipe receives a brine stream from an MEG reclaimer flash drum. Flow through the large bore pipe and the strainer is slow, allowing for solids to settle within the large bore pipe. Accumulated salt is discharged from the bottom of the large bore pipe. In some implementations, the bottom of the large bore pipe is sloped downward toward the brine discharge location. An outlet stream with decreased salt content (in comparison to the brine stream received from the flash drum) is discharged downstream of the strainer and returned to the flash drum. In some implementations, fine particles pass through the strainer (while larger particles are prevented from passing through the strainer), and the fine particles return to the flash drum, where they can act as seeds (for example, nucleation sites) for salt precipitation in the flash drum. Make-up water (with less salt content than the brine stream from the flash drum, and in some implementations, with less salt content than the outlet stream with decreased salt content) can be supplied downstream of the strainer. The same nozzle used to provide make-up water can also be used for flushing to discharge brine from the large bore pipe. In some implementations, a duplicate apparatus is installed in parallel, such that the MEG reclamation unit can run continuously. For example, one apparatus is used for solid separation (connected to the MEG reclaimer flash drum) while the other apparatus is flushed to discharge brine, and the operating modes can be alternated without requiring down time.

The subject matter described in this disclosure can be implemented in particular implementations, so as to realize one or more of the following advantages. Solids can be removed for MEG reclamation without the use of cyclonic separation or centrifugation, which can require several equipment in relatively complicated configurations. The subject matter described can be implemented to remove bulk solids from liquid streams, especially in cases where large volumes of solid contaminants are present, for example, up to 7.5 weight percent (wt. %) of solid contaminants.

Figure 1A:
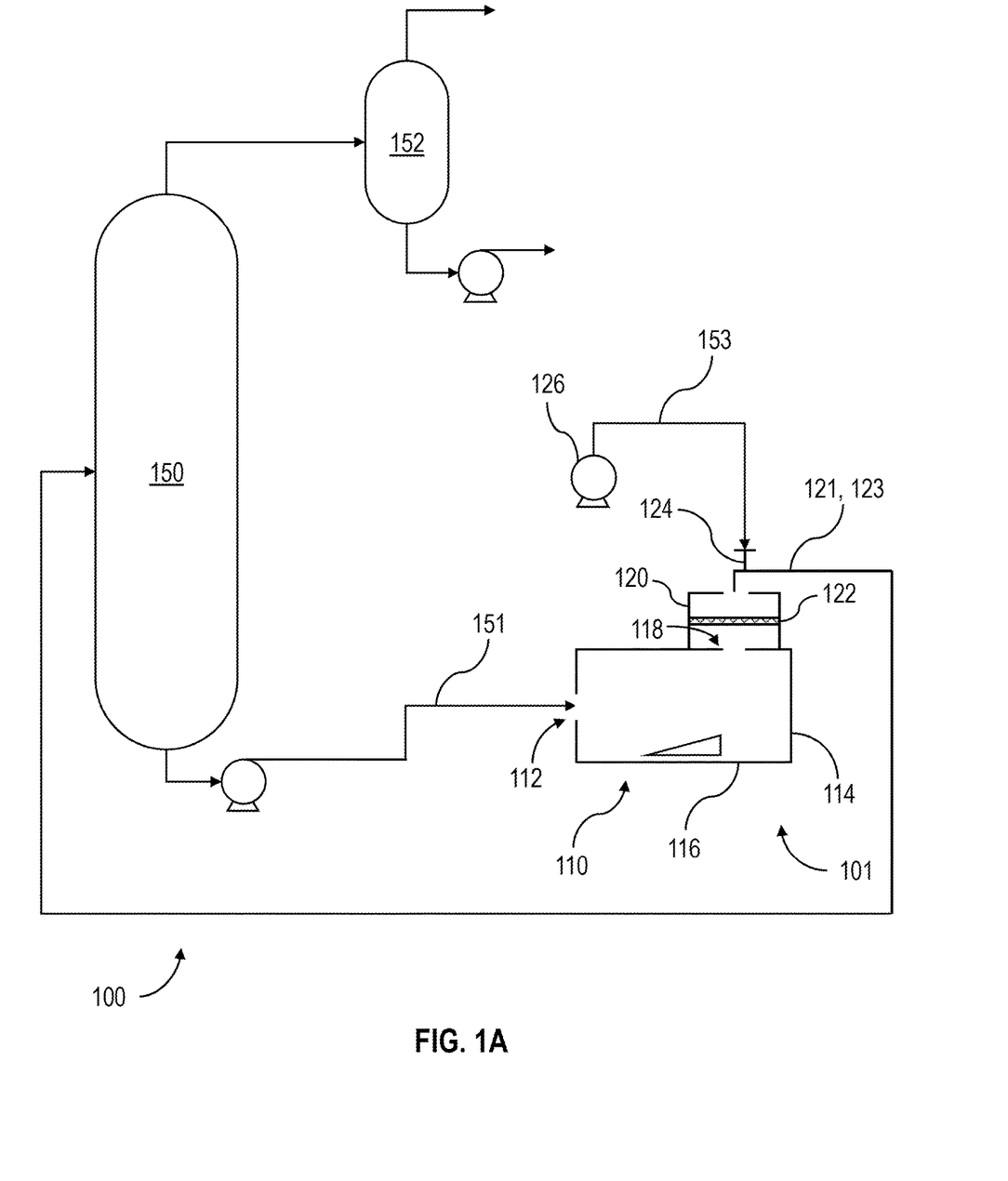
FIG. 1A is a schematic diagram of an example system for removing solids in glycol reclamation.

FIG. 1A is a schematic diagram of a system 100 for removing solids in glycol reclamation. The system 100 includes a solids removal apparatus 101. The solids removal apparatus 101 includes a first tubular 110, a second tubular 120, and a strainer 122. The first tubular 110 includes an open end 112, a closed end 114, and a wall 116 spanning from the open end 112 to the closed end 114. The closed end 114 is opposite the open end 112. The wall 116 defines an opening 118 on a lateral surface of the wall 116. The second tubular 120 is connected to the opening 118 and protrudes from the first tubular 110. The open end 112 is configured to receive a brine stream 151 from a reclaimer flash drum 150 of an ethylene glycol (MEG) reclaimer unit. The brine stream 151 includes solid material, such as salt. Some examples of salt expected in the brine stream 151 includes sodium chloride, potassium chloride, calcium chloride, and calcium carbonate. The second tubular 120 is configured to discharge an outlet stream 121. The strainer 122 is disposed within the second tubular 120.

The MEG reclaimer flash drum 150 separates a salty MEG stream into a salt-free, lean MEG stream and the brine stream 151. The brine stream 151 flows from the MEG reclaimer flash drum 150 to the solids removal apparatus 101. In some implementations, the brine stream 151 is pumped by a brine pump from the MEG reclaimer flash drum 150 to the solids removal apparatus 101. In some implementations, the brine stream 151 operates at a temperature in a range of from approximately 212 degrees Fahrenheit (° F.) to approximately 290° F. The solids removal apparatus 101 removes at least a portion of the solids from the brine stream 151 and return the outlet stream 121 to the MEG reclaimer flash drum 150.

The strainer 122 is configured to prevent at least a portion of the solid material of the brine stream 151 from flowing through the strainer 122, such that the outlet stream 121 discharging from the second tubular 120 has a solids content that is less than a solids content of the brine stream 151. In some implementations, the strainer 122 defines multiple perforations that are sized to allow solid material having a maximum dimension of up to approximately 1 millimeter (mm) to pass through the strainer 122 while preventing solid material having a dimension of greater than approximately 1 mm from passing through the strainer 122. In some implementations, the strainer 122 defines multiple perforations that are sized to allow solid material having a maximum dimension of up to approximately 0.5 mm to pass through the strainer 122 while preventing solid material having a dimension of greater than approximately 0.5 mm from passing through the strainer 122. In some implementations, the size of the perforations defined by the strainer 122 are in a range of from 20 mesh to 30 mesh. In some implementations, the strainer 122 is made of stainless steel, such as 316L class stainless steel. If the brine stream 151 is expected to be chloride-rich (for example, having a chloride concentration of greater than 500 parts per million (ppm)), the strainer 122 can be made of a stainless steel that is resistant to chloride corrosion. In some implementations, the strainer 122 is at least 1 mm thick.

In some implementations, the second tubular 120 is in fluid communication with the reflux flash drum 152, such that the solid material having the maximum dimension of up to approximately 0.5 mm or up to approximately 1 mm is allowed to flow to the MEG reclaimer flash drum 150 with the outlet stream 121. In some implementations, as shown in FIG. 1A, the entirety of the strainer is positioned above the first tubular 110 with respect to gravity. This orientation can help to separate solids from the brine stream 151 flowing through the strainer 122 due to the effects of gravity. This orientation can also mitigate clogging of the perforations defined by the strainer 122, as solid material will tend to fall back down into the first tubular 110 instead of remaining stuck in the perforations of the strainer 122. In some implementations, the second tubular 120 has an inner diameter that is less than an inner diameter of the first tubular 110.22

In implementations where finer solid material (for example, the solid material having a maximum dimension of up to approximately 1 mm) is allowed to pass through the strainer 122 and exit the apparatus 101 with the outlet stream 121, the outlet stream 121 can be recycled to the MEG reclaimer flash drum 150. Such solid material can serve as seeds for crystallizing salt into larger particles, which can subsequently be separated out (for example, by the strainer 122) once flowed back to the apparatus 101.

In some implementations, the apparatus 101 includes a flow line 123 from the second tubular 120 to the reflux flash drum 152. In such implementations, the flow line 123 is configured to flow the outlet stream 121 from the second tubular 120 to the reflux flash drum 152. In some implementations, the flow line 123 connects the second tubular 120 to the MEG reclaimer flash drum 150. In such implementations, the flow line 123 is configured to flow the outlet stream 121 from the second tubular 120 to the MEG reclaimer flash drum 150. In some implementations, the flow line 123 includes a nozzle 124 configured to supply make-up water 153 downstream of the strainer 122. In some implementations, the make-up water 153 has a solids content that is less than the solids content of the brine stream 151. In some implementations, the make-up water 153 has a solids content that is less than the solids content of the outlet stream 121. In some implementations, the nozzle 124 is configured to connect to a flush pump 126 for backflow flushing of the first tubular 110. After solids have accumulated within the first tubular 110 for a time period (for example, approximately two days) or up to a maximum amount (for example, approximately 2,000 pounds of salt), the first tubular 110 can be flushed to remove the accumulated solids.

In some implementations, the first tubular 110 is a large bore diameter pipe. In some implementations, an inner diameter of the first tubular 110 is at least 8 inches, at least 12 inches, at least 16 inches, or at least 20 inches. In some implementations, the inner diameter of the first tubular 110 is uniform along a longitudinal length of the first tubular 110. In some implementations, an inner diameter of the first tubular 110 is determined based on a design flow rate of the brine stream 151 flowed to the open end 112 of the first tubular 110. The inner diameter of the first tubular 110 can be designed to be larger for greater design flow rates of the brine stream 151. The large cross-sectional flow area of the first tubular 110 can decrease the velocity of the brine stream 151 flowing through the first tubular 110. The decreased velocity of the brine stream 151 through the first tubular 110 can allow for improved separation of solids from the brine stream 151. For example, for a design flow rate of the brine stream 151 in a range of from approximately 3 gallons per minute (gpm) to approximately 8 gpm, an inner diameter of the first tubular 110 can be in a range of from 8 inches to 12 inches. For example, for a design flow rate of the brine stream 151 in a range of from approximately 10 gpm to approximately 20 gpm, an inner diameter of the first tubular 110 can be in a range of from 16 inches to 20 inches. For example, a ratio of a flow rate of the brine stream 151 to an inner diameter of the first tubular 110 can be in a range of from approximately 3 gallons per minute per foot (gpm/ft) to approximately 12 gpm/ft.

Figure 1B:
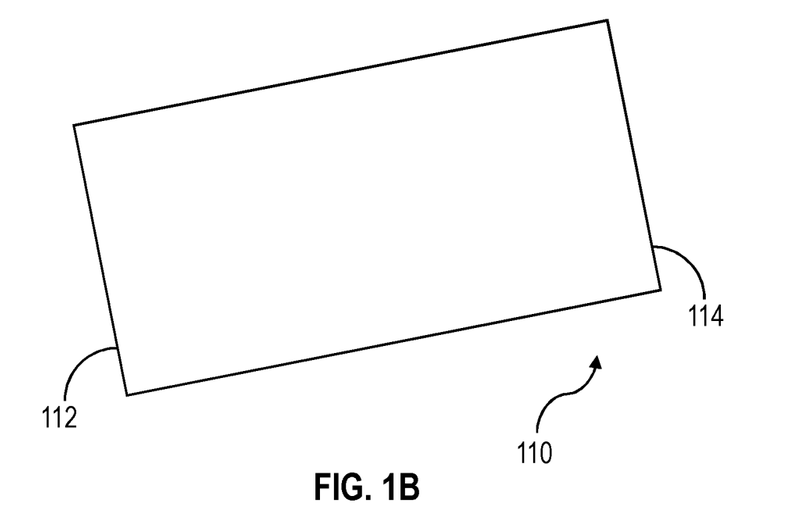
FIG. 1B is a schematic diagram of an example large bore tubular of the system of FIG. 1A.
Figure 1C:
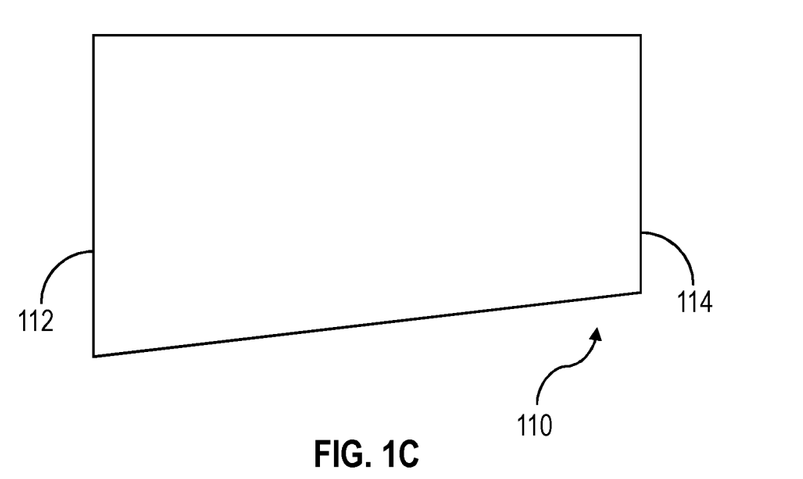
FIG. 1C is a schematic diagram of an example large bore tubular of the system of FIG. 1A.

In some implementations, as shown in FIG. 1B, the entire first tubular 110 is sloped. In such implementations, the open end 112 and the closed end 114 have the same diameter. In some implementations, as shown in FIG. 1C, the bottom of the first tubular 110 is sloped. In such implementations, the open end 112 and the closed end 114 have different diameters. Although the open end 112 is shown as having a larger diameter than the closed end 114 in FIG. 1C, in some implementations, the open end 112 has a smaller diameter than the closed end 114, and the bottom slopes downwardly toward the closed end 114. In the implementations shown in FIGS. 1B and 1C, solids within the first tubular 110 tend to slide down the slope due to gravity. In some implementations, the slope of the entire first tubular 110 or the bottom of the first tubular 110 is at least 1:320. In some implementations, the slope of the entire first tubular 110 or the bottom of the first tubular 110 is at least 1:12. In some implementations, the slope of the entire first tubular 110 or the bottom of the first tubular 110 is in a range of from 1:320 to 1:12.

Figure 1D:
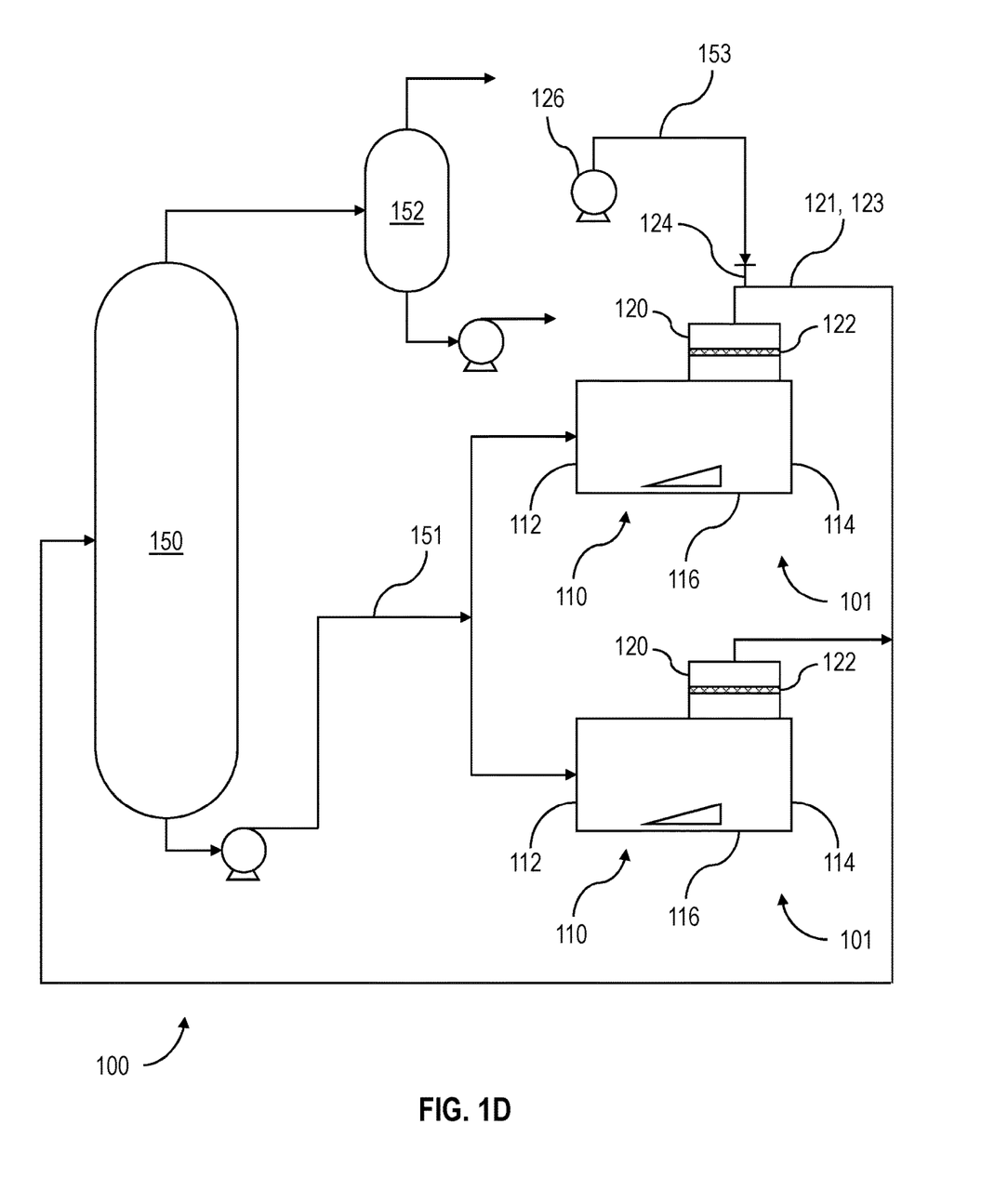
FIG. 1D is a schematic diagram of an example system for removing solids in glycol reclamation

FIG. 1D is a schematic diagram of the system 100 including multiple apparatuses 101 for removing solids in glycol reclamation. In some implementations, as shown in FIG. 1D, the system 100 includes multiple apparatuses 101 in parallel. Each of the open ends 112 are configured to receive the brine stream 151 from the MEG reclaimer flash drum 150. Each of the second tubulars 120 can be configured to discharge an outlet stream 121 for flowing back to the MEG reclaimer flash drum 150. In such configurations, the MEG reclamation process can run continuously without interruption. For example, one of the apparatuses 101 is used to remove solids from the brine stream 151 while the other of the apparatuses 101 is flushed to remove accumulated solids, for example, from the first tubular 110. The modes can then be switched.

Figure 2:
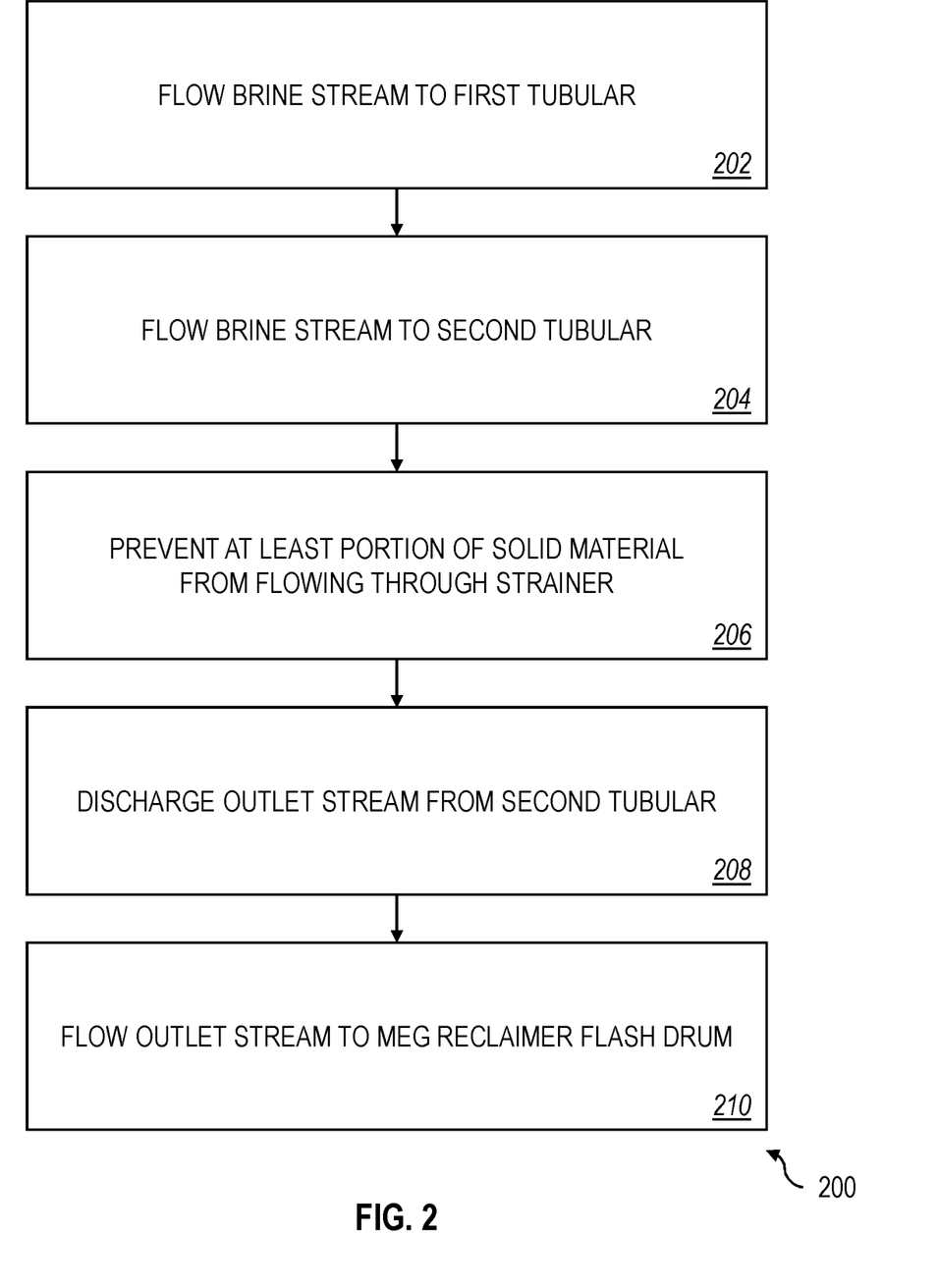
FIG. 2 is a flow chart of an example method for removing solids in glycol reclamation.

FIG. 2 is a flow chart of a method 200 for removing solids in glycol reclamation. The apparatus 101 can be used, for example, to implement method 200. At step 202, a brine stream (such as the brine stream 151) is flowed from a reclaimer flash drum (such as the MEG reclaimer flash drum 150) of an ethylene glycol reclaimer unit to a first tubular (such as the first tubular 110). As described previously, the brine stream 151 includes solid material, such as salt. In some implementations, the brine stream 151 is flowed at step 202 at a flow rate that satisfies a ratio of the flow rate to an inner diameter of the first tubular 110 being in a range of from approximately 3 gpm/ft to approximately 12 gpm/ft.

At step 204, the brine stream 151 is flowed from the first tubular 110 to a second tubular (such as the second tubular 120) that is connected to an opening (such as the opening 118) defined on a lateral surface of the first tubular 110 and protruding from the first tubular 110.

At step 206, at least a portion of the solid material is prevented, by a strainer (such as the strainer 122) disposed within the second tubular 120, from flowing through the strainer 122 as the brine stream 151 flows through the strainer 122. In some implementations, the strainer 122 defines perforations sized to allow solid material having a maximum dimension of up to approximately 1 mm to pass through the strainer while preventing solid material having a dimension greater than approximately 1 mm from passing through the strainer 122 at step 206. In some implementations, the strainer 122 defines perforations sized to allow solid material having a maximum dimension of up to approximately 0.5 mm to pass through the strainer while preventing solid material having a dimension greater than approximately 0.5 mm from passing through the strainer 122 at step 206.

At step 208, an outlet stream (such as the outlet stream 121) is discharged from the second tubular 120. As described previously, the outlet stream 121 has a solids content that is less than a solids content of the brine stream 151. In some implementations, the solids content of the outlet stream 121 is approximately 5% or less of the solids content of the brine stream 151.

At step 210, the outlet stream 121 is flowed to the MEG reclaimer flash drum 150. In some implementations, make-up water (such as the make-up water 153) is flowed to a flow line (such as the flow line 123) connecting the second tubular 120 to the MEG reclaimer flash drum 150. In some implementations, the make-up water 153 has a solids content that is less than the solids content of the brine stream 151. In some implementations, the make-up water 153 has a solids content that is less than the solids content of the outlet stream 121. In some implementations, the first tubular 110 is backflow flushed (for example, with the flush pump 126) using the flow line 123.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A glycol reclamation system comprising:
a reclaimer flash drum; and
a solids removal apparatus in fluid communication with the reclaimer flash drum, the solids removal apparatus comprising:
a first tubular comprising:
an open end in fluid communication with the reclaimer flash drum for receiving a brine stream from the reclaimer flash drum;
a closed end opposite the open end; and
a wall spanning from the open end to the closed end, the wall defining an opening on a lateral surface of the wall;

a second tubular in fluid communication with the opening and protruding from the first tubular, the second tubular having an inner diameter that is less than an inner diameter of the first tubular, the second tubular having an outlet in fluid communication with the reclaimer flash drum for discharging an outlet stream; and a strainer disposed between the opening and the outlet within the second tubular and being capable of removing at least some solids from the brine stream such that the outlet stream has fewer solids than the brine stream.

2. The system of claim 1, wherein the strainer defines a plurality of perforations sized to allow solid material having a maximum dimension of up to approximately 1 millimeter (mm) to pass through the strainer while preventing solid material having a dimension of greater than approximately 1 mm from passing through the strainer, such that the solid material having the maximum dimension of up to approximately 1 mm is allowed to flow to the reclaimer flash drum with the outlet stream.

3. The system of claim 2, further comprising a flow line from the second tubular to the reclaimer flash drum, the flow line comprising a nozzle capable of supplying make-up water downstream of the strainer.

4. The system of claim 3, further comprising a flush pump fluidically connected to the nozzle.

5. The system of claim 1, wherein the inner diameter of the first tubular is at least approximately 8 inches.

\* \* \* \* \*